United States Patent
Ruggiero et al.

(12)

(10) Patent No.: US 6,258,804 B1
(45) Date of Patent: Jul. 10, 2001

(54) TRIAZEPINONES, PROCESS FOR THEIR PREPARATION AND THEIR THERAPEUTIC APPLICATION

(75) Inventors: Daniel Ruggiero, Sainte Consorce; Nicolas Wiernsperger, Orlienas; Gérard Patereau, Maurepas; Gérard Moinet, Orsay, all of (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/600,294

(22) PCT Filed: Jan. 11, 1999

(86) PCT No.: PCT/EP99/00100

§ 371 Date: Jul. 14, 2000

§ 102(e) Date: Jul. 14, 2000

(87) PCT Pub. No.: WO99/36396

PCT Pub. Date: Jul. 22, 1999

(30) Foreign Application Priority Data

Jan. 14, 1999 (FR) .................................................. 98 00321

(51) Int. Cl.⁷ ........................ C07C 255/02; A61K 31/55
(52) U.S. Cl. ............................................ 514/183; 540/492
(58) Field of Search ............................. 514/183; 540/492

(56) References Cited

U.S. PATENT DOCUMENTS 2,961,377  11/1960  Shapiro et al. ........................ 167/65

OTHER PUBLICATIONS

Uyeda et al. (Biocontrol Sci. (1997), 2(1), 35–38) Abstract.*
Chemical Abstracts, vol. 127, No. 3, Jul. 21, 1997 Columbus, Ohio, US; abstract No. 28696w, Masaru Uyeda et al: "Formartion of chlorhexidine degradation intermediate through pyryvate incorporation by Pseudomonas sp. No. A–3" p. 28; XP002078367 & Biocontrol Sci., vol. 2, No. 1, 1997, pp. 35–38.
F. E. King et al: "Benzimidazole analogues of paludrine" Journal of the Chemical Society, 1948, pp. 1366–1371, XP002078366.
B. Agai et al: "Condensed 1,3,5–triazepines. III. Derivatives of 4,5–dihydro–(1,3,5)triazepino(1,2–a)benzim idazoles" Tetrahedron, vol. 32, No. 7, 1976, pp. 839–842, XP002078365.

* cited by examiner

*Primary Examiner*—Bruce Kifle
(74) *Attorney, Agent, or Firm*—Millen White Zelano & Branigan

(57) ABSTRACT

Described are compound of the formula (I) defined herein which are useful, for example, in the treatment of diabetes. Also described is a method for preparing the compounds.

5 Claims, No Drawings

TRIAZEPINONES, PROCESS FOR THEIR PREPARATION AND THEIR THERAPEUTIC APPLICATION

The present invention relates to novel triazepine derivatives, to a process for their preparation and to pharmaceutical compositions containing them.

The invention relates more specifically to novel triazepine derivatives which are useful in therapy for inhibiting the reaction of glucose or of its oxidation products (α-dicarbonyl derivatives such as glyoxal or methylglyoxal) with the amine groups of proteins, and which consequently find an application in the treatment of diabetes and its complications.

The subject of the present invention is thus compounds of general formula:

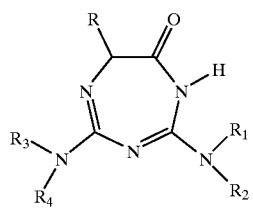

(I)

in which:

R is chosen from a hydrogen atom, a methyl group and a group of formula:

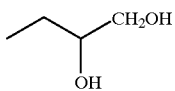

and $R_1$, $R_2$, $R_3$ and $R_4$ are chosen, independently of each other, from:

a) a hydrogen atom, b) a $C_1$–$C_8$ alkyl, cyclo($C_3$–$C_8$)alkyl, cyclo($C_3$–$C_8$)alkyl($C_1$–$C_8$)alkyl, cyclo($C_3$–$C_8$)alkyloxy($C_1$–$C_8$) alkyl, cyclo($C_3$–$C_8$)alkyl($C_1$–$C_8$)alkoxy($C_1$–$C_8$) alkyl, ($C_1$–$C_8$)alkoxy($C_1$–$C_8$)alkyl, ($C_1$–$C_8$) hydroxyalkyl, ($C_6$–$C_{14}$) aryl, ($C_6$–$C_{14}$) heteroaryl, hetero($C_6$–$C_{14}$)aryl($C_1$–$C_8$)alkyl, ($C_6$–$C_{14}$)aryl ($C_1$–$C_8$)alkyl, ($C_6$–$C_{14}$)aryl($C_1$–$C_8$)alkyl($C_6$–$C_{14}$) aryl, ($C_6$–$C_{14}$)aryloxy($C_1$–$C_8$)alkyl or ($C_6$–$C_{14}$)aryl ($C_1$–$C_8$)alkyloxy($C_1$–$C_8$)alkyl group, it being possible for the various aryl, cycloalkyl and heteroaryl groups to be substituted themselves with 1 to 3 substituents chosen from a ($C_1$–$C_8$) alkyl group, a $C_1$–$C_8$ alkoxy group, a halogen chosen from fluorine, chlorine, bromine and iodine, and a trifluoromethoxy, hydroxyl, cyano, nitro, amino, carbamoyl, $C_1$–$C_8$ alkylamino, ($C_1$–$C_8$) alkylthio ($C_1$–$C_8$)alkylsulphinyl, $C_1$–$C_8$ alkylsulphonyl, sulphonylamino or sulphamoyl ($C_1$–$C_8$) alkylcarbonylamino group, it being possible for two of these groups to form a methylenedioxy group;

it being possible for $R_1$ and $R_2$ as well as $R_3$ and $R_4$ to form, with the nitrogen which bears them, a group of general formula:

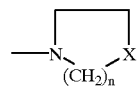

(1)

in which n represents a number from 1 to 4 and X is chosen from —$CH_2$—, —O—, —S—, —NH— and —NR'—, R'having the meaning given for $R_1$ in b);

c) a group of formula:

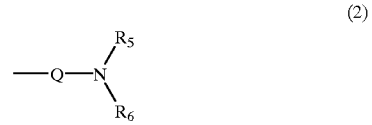

(2)

in which Q represents a linear or branched $C_2$–$C_{14}$ alkylene group;

$R_5$ and $R_6$ are chosen, independently of each other, from a hydrogen atom and a group mentioned above in b);

it being possible for $R_5$ and $R_6$ also to form, with the nitrogen which bears them, a group of general formula (1);

d) a bicyclic amine residue of fused or bridged type, and their salts with pharmaceutically acceptable acids.

The $C_1$–$C_8$ alkyl groups can be linear or branched. As examples, mention may be made of methyl, ethyl, isopropyl, butyl, isobutyl, tert-butyl and pentyl groups.

The $C_1$–$C_8$ alkoxy groups can similarly be linear or branched. As examples, mention may be made of methoxy, ethoxy, propoxy, isopropoxy, butoxy, isobutoxy and pentoxy groups.

The term aryl group is understood to refer to a monocyclic, bicyclic or tricyclic group containing from 6 to 14 carbon atoms. As examples of an aryl group mention may be made of phenyl, α-naphthyl, β-naphthyl and fluorenyl groups.

The heteroaryl groups can be chosen in particular from pyridyl, pyrimidyl, pyrrolyl, furyl, thienyl, quinolyl, indolyl, benzothienyl, benzofuryl, benzopyranyl, benzothiopyranyl, dibenzofuryl, carbazolyl and benzothiazinyl groups.

The expression bicyclic amine residue of fused or bridged type is understood to denote residues of the type:

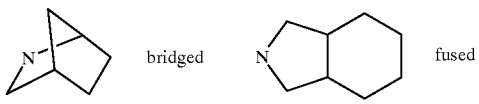

The compounds of general formula (I) contain basic nitrogen atoms and can be salified with inorganic or organic acids. Examples of salts, with acids, of the compounds of general formula (I) include pharmaceutically acceptable salts such as, in a non-exhaustive manner, hydrochloride, hydrobromide, sulphate, succinate, maleate, fumarate, malate, tartrate and sulphonates such as methanesulphonate, benzenesulphonate and toluenesulphonate.

The compounds of formula I can be prepared by reaction of α-keto aldehydes of general formula:

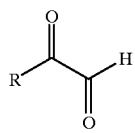
(II)

with biguanides of general formula:

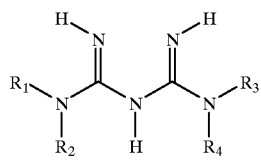
(III)

Biguanides of formula (III) are described in particular in U.S. Pat. No. 2,455,896, FR-A-2,085,665, FR-A-1,518,398, FR-A-2,230,347 and U.S. Pat. No. 2,961,377.

This reaction can be carried out in an alcohol of low molecular weight (for example methanol) or, more advantageously, in water.

The structure of the compounds obtained was confirmed by analysis of the $^1H$, $^{15}N$ and $^{13}C$ spectra.

The example which follows illustrates the preparation of the compounds of formula (I).

EXAMPLE 1

Preparation of 2-amino-4-dimethylamino-7-methyl-5,7-dihydro(1,3,5)triazepin-6-one (and hydrochloride)

25.8 g (0.2 mol) of base N,N-dimethylbiguanide (metformine) and 100 ml of water are introduced into a 250 ml three-necked flask; after complete dissolution, the solution is cooled and, while maintaining the internal temperature between 0 and +5°, 34 ml (0.210 mol) of aqueous 40% methylglyoxal (pyruvaldehyde) solution are run in.

The mixture is stirred for 1 hour at +5° C. A crystalline precipitate forms. The mixture is stirred for a further 4 hours at +20° C. The product is filtered off on a sinter funnel, washed with water and dried under vacuum. A pale cream-white product weighing 18.2 g (yield: 50%) and melting at 264 . 266° C. (Köfler bank) is obtained. It is recrystallized from dimethylformamide. Its hydrochloride was prepared, and this melts at 260–262° C. (Köfler bank).

The compounds of the invention can be used in the treatment of diabetes and its complications.

The chronic complications of diabetes are due to the formation of Advanced Glycosylation End-Products, known as AGE's, derived from the glycoxidation reaction between glucose, its oxidation derivatives and the amino functions of proteins, including the so-called Maillard reactions of glycation of glyoxal, for example.

Compounds of biguanide type, such as metformine, inhibit these reactions by interfering in the reactions between the amino groups of proteins and the α-dicarbonyl derivatives of glucose, in particular methylglyoxal.

Now, the theory of glyoxidation in the pathogenesis of diabetes complications involves several metabolic routes:

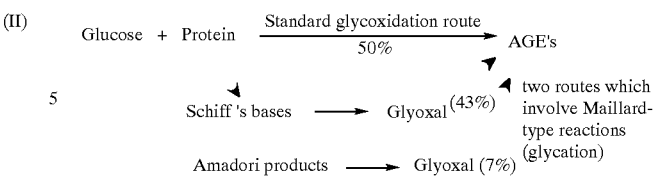

It is thus seen that 50% of the AGE products in the body, which are responsible for the chronic complications of diabetes, are derived from reactions involving glyoxal.

The value of the compounds of formula (I) is that they are capable of inhibiting the so-called Maillard reactions by means of a "scavenging" effect on α-dicarbonyl derivatives such as glyoxal, and these compounds therefore have an antiglycation effect.

This effect of inhibiting the Maillard reaction by the compounds according to the invention has been studied in vitro by assaying the ketamines ("fructosamine") produced during the incubation of albumin with methylglyoxal in the presence or absence of a compound according to the invention.

A bovine albumin solution at 6.6 mg/ml in 0.2M pH 7.4 phosphate buffer is incubated with 1 mM methylglyoxal in the presence or absence of 2-amino-4-dimethylamino-7-methyl-5,7-dihydro(1,3,5)triazepin-6-one at a concentration of 1 mM. The incubation is carried out under sterile conditions, at 37° C. for 6 days. At the end of the incubation period, the amount of ketamines formed is measured with a commercially available fructosamine assay kit, the "FRA" kit, which has the product reference: 0757055, Produits Roche S. A.) according to the manufacturer's instructions. Under these experimental conditions, the level of fructosamine after incubation of the albumin with methylglyoxal in the presence of 2-amino-4-dimethylamino-7-methyl-5,7-dihydro(1,3,5)triazepin-6-one is 31% less than that observed when the albumin is incubated with methylglyoxal in the absence of this triazepinone.

The subject of the present invention is thus pharmaceutical compositions comprising, as active principle, a compound according to the invention.

The pharmaceutical compositions according to the invention can be provided in forms intended for parenteral, oral, rectal, permucous or percutaneous administration.

They will thus be provided in the form of solutions or suspensions for injection or multi-dose bottles, in the form of plain or coated tablets, sugar-coated tablets, wafer capsules, gelatin capsules, pills, cachets, powders, suppositories or rectal capsules, or solutions or suspensions, for percutaneous use in a polar solvent, or for permucous use.

The excipients which are suitable for such administrations are derivatives of cellulose or microcrystalline cellulose, alkaline-earth metal carbonates, magnesium phosphate, starches, modified starches and lactose for the solid forms.

For rectal use, cocoa butter or polyethylene glycol stearates are the preferred excipients.

For parenteral use, water, aqueous solutions, physiological saline and isotonic solutions are the vehicles used most conveniently.

The dosage can vary within a wide range depending on the therapeutic indication and the route of administration, as well as the age and the weight of the individual.

What is claimed is:

1. A compound of the formula (I):

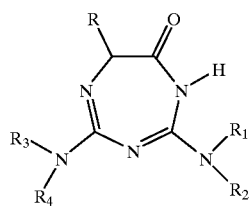

in which:

R is a hydrogen atom, a methyl group or a group of the formula:

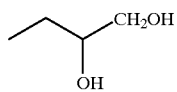

and $R_1$, $R_2$, $R_3$ and $R_4$ are, independently of each other:
a) a hydrogen atom, or
b) a $C_1$–$C_8$ alkyl, cyclo($C_3$–$C_8$)alkyl, or cyclo($C_3$–$C_8$) alkyl($C_1$–$C_8$)alkyl group, the cycloalkyl groups optionally being substituted with 1 to 3 substituents chosen from a ($C_1$–$C_8$) alkyl group, a $C_1$–$C_8$ alkoxy group, a halogen chosen from fluorine, chlorine, bromine and iodine, and a trifluoromethoxy, hydroxyl, cyano, nitro, amino, carbamoyl, ($C_1$–$C_8$) alkyl, $C_1$–$C_8$ alkylamino, ($C_1$–$C_8$)alkylthio ($C_1$–$C_8$) alkylsulphinyl, $C_1$–$C_8$ alkylsulphonyl, sulphonylamino or sulphamoyl ($C_1$–$C_8$) alkylcarbonylamino group, or a salt thereof with a pharmaceutically acceptable acid.

2. Compound according to claim 1, which is 2-amino-4-dimethylamino-7-methyl-5,7-dihydro (1,3,5)triazepin-6-one, or its salt with a pharmaceutically acceptable acid.

3. A process for preparing a compound according to claim 1, in which a compound of formula:

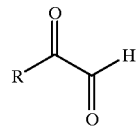

is reacted with a biguanide of formula:

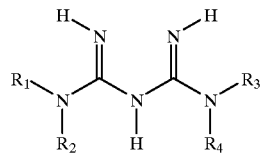

R, $R_1$, $R_2$, $R_3$, and $R_4$ having the meaning given in claim 1.

4. A pharmaceutical composition comprising, as active principle, an effective amount of a compound according to claim 1 and a pharmaceutically acceptable carrier.

5. A pharmaceutical composition comprising, as active principle, an effective amount of a compound according to claim 2 and a pharmaceutically acceptable carrier.

* * * * *